(12) United States Patent
Reyes et al.

(10) Patent No.: US 7,971,268 B2
(45) Date of Patent: Jul. 5, 2011

(54) CONTROLLED DEFLECTION GOGGLE

(75) Inventors: Carlos Reyes, Rancho Santa Margarita, CA (US); James Nelson Castro, Laguna Niguel, CA (US); Hans Moritz, Foothill Ranch, CA (US); Steve Oldham, Corona, CA (US)

(73) Assignee: Oakley, Inc., Foothill Ranch, CA (US)

( * ) Notice: Subject to any disclaimer, the term of this patent is extended or adjusted under 35 U.S.C. 154(b) by 169 days.

(21) Appl. No.: 12/359,175

(22) Filed: Jan. 23, 2009

(65) Prior Publication Data
US 2010/0186153 A1 Jul. 29, 2010

(51) Int. Cl.
*A61F 9/02* (2006.01)
*A61F 9/04* (2006.01)

(52) U.S. Cl. .................................. 2/15; 2/426

(58) Field of Classification Search .............. 351/86, 351/51, 52, 44, 47, 57, 48, 58, 41; 2/15, 2/12, 13, 426–429, 438, 439, 441–446
See application file for complete search history.

(56) References Cited

U.S. PATENT DOCUMENTS

| | | | |
|---|---|---|---|
| 916,109 A | 3/1909 | Cook | |
| 2,274,791 A | 3/1942 | Huggins | |
| 2,288,423 A | 6/1942 | Root | |
| 2,444,498 A | 7/1948 | Cochran | |
| 2,612,639 A | 10/1952 | Christensen et al. | |
| 2,615,162 A | 10/1952 | Christensen et al. | |
| 2,618,782 A * | 11/1952 | Christensen et al. | 2/436 |
| 2,619,643 A | 12/1952 | Christensen et al. | |
| 2,619,644 A | 12/1952 | Christensen et al. | |
| 3,016,797 A | 1/1962 | Liautaud | |
| 3,233,249 A | 2/1966 | Baratelli et al. | |
| 4,240,718 A * | 12/1980 | Wichers | 351/62 |
| 4,290,673 A | 9/1981 | Yamamoto | |
| 4,317,240 A * | 3/1982 | Angerman et al. | 2/436 |
| 4,443,893 A | 4/1984 | Yamamoto | |

(Continued)

FOREIGN PATENT DOCUMENTS

GB 127410 5/1919

(Continued)

OTHER PUBLICATIONS

International Search Report and Written Opinion received in corresponding PCT Application No. PCT/US2010/021033, mailed Feb. 25, 2010, 14 pages.

*Primary Examiner* — Bobby H Muromoto, Jr.
(74) *Attorney, Agent, or Firm* — Knobbe, Martens, Olson & Bear, LLP

(57) ABSTRACT

A goggle is provided that can include a goggle frame and a bend control component. The goggle frame can define opposing lateral portions and a central portion. The goggle frame can include a bridge disposed at the central portion of the goggle frame. The goggle frame can be generally flexible upon exertion of a bending force on the goggle frame. The bend control component can extend along the bridge of the goggle frame. The bend control component can be configured to enhance flexural strength of the goggle at a bridge thereof for reducing bending of the goggle frame at the bridge. In some embodiments, the bend control component is formed separately from the goggle frame. In other embodiments, the bend control component can be secured to the frame using fasteners and/or one or more protrusions and corresponding recesses.

32 Claims, 12 Drawing Sheets

U.S. PATENT DOCUMENTS

| | | | |
|---|---|---|---|
| 4,689,838 A | 9/1987 | Angermann et al. | |
| 4,730,915 A * | 3/1988 | Jannard | 351/47 |
| 5,220,689 A | 6/1993 | Miller | |
| 5,410,763 A | 5/1995 | Bollé | |
| 5,657,106 A | 8/1997 | Herald, Jr. et al. | |
| 5,689,834 A | 11/1997 | Wilson | |
| 5,805,261 A * | 9/1998 | Houston et al. | 351/126 |
| D405,102 S | 2/1999 | Moritz et al. | |
| 6,009,564 A * | 1/2000 | Tackles et al. | 2/436 |
| 6,049,917 A | 4/2000 | Ryden | |
| 6,056,399 A * | 5/2000 | Jannard et al. | 351/126 |
| D428,039 S | 7/2000 | Thixton | |
| 6,427,254 B1 | 8/2002 | Gardner | |
| D505,150 S * | 5/2005 | Yee et al. | D16/314 |
| 6,929,364 B1 * | 8/2005 | Jannard | 351/126 |
| D513,761 S * | 1/2006 | Yee et al. | D16/335 |
| 7,210,776 B2 * | 5/2007 | Jannard et al. | 351/41 |
| 7,222,959 B2 * | 5/2007 | Jannard | 351/124 |
| 7,367,669 B2 * | 5/2008 | Jannard et al. | 351/41 |
| 7,686,449 B2 * | 3/2010 | Jannard et al. | 351/124 |
| 2004/0117898 A1 * | 6/2004 | Penque et al. | 2/431 |
| 2007/0200997 A1 * | 8/2007 | Jannard et al. | 351/126 |
| 2010/0085533 A1 * | 4/2010 | Calilung et al. | 351/90 |
| 2010/0186153 A1 * | 7/2010 | Reyes et al. | 2/427 |

FOREIGN PATENT DOCUMENTS

| | | |
|---|---|---|
| GB | 129048 | 7/1919 |
| WO | WO 97/41815 A1 | 11/1997 |
| WO | WO 2007/057470 A1 | 5/2007 |

* cited by examiner

CONTROLLED DEFLECTION GOGGLE

BACKGROUND

1. Field of the Inventions

The present inventions relate generally to eyewear products. More specifically, the present inventions relate to methods and apparatuses for controlling the deflection of a lens in order to optimize the optical quality of the lens and to provide a customized fit for the wearer.

2. Description of the Related Art

A wide variety of improvements have been made in recent years in the eyewear field, particularly with respect to eyewear intended for use in active sports, including goggles and sunglasses. Many improvements have been made with respect to lens molding technology and fashion sunglasses as well. These improvements have been incorporated into eyewear having both a unitary lens and dual lens design. As a result, modern active sport eyewear is functionally superior to its predecessor eyewear in numerous ways, such as by maximizing interception of peripheral light, reducing optical distortion, and increasing the wearer's comfort level.

For example, lens designs for both dual and unitary eyewear designs can provide full side-to-side range of vision and good lateral eye protection while providing superior optical performance. More particularly, in a unitary lens system, the angle of incidence from the wearer's eye to the posterior lens surface changes as the wearer's line of sight turns in either the vertical or the horizontal planes. This results in disparate refraction between light entering closer to the front of the lens and peripheral light entering at the lateral ends. To address this source of prismatic distortion, U.S. Pat. No. 4,859,048 discloses tapering the thickness of the lens from the medial portion toward the lateral edge, the entirety of the disclosure of which is incorporated by reference herein.

Further, various improvements have also been made in lens mounting technology that allow mounted lenses to retain their superior optical characteristics provided by their as-molded geometry. For example, the dual lens "Racing Jacket" manufactured by Oakley, Inc. incorporates a lens suspension design that mitigates any mounting stresses on the lens in order to allow the lens to float and retain its as-molded geometry. Such systems are disclosed in U.S. Patent Application No. 61/078,326, titled Floating Lens Mounting System, filed Jul. 3, 2008, the entire disclosure of which is incorporated herein by reference.

Finally, numerous modifications have been made to eyeglass and goggle products in an effort to make these products more comfortable for the wearer. For example, different materials have been used in the manufacture of frames and lenses in order to decrease the weight and improve the touch and feel of these products. These technological improvements can be incorporated into any variety of dual or unitary lens designs, whether for eyeglass or goggle products, in order to provide a wearer with a comfortable, optically superior eyewear product.

SUMMARY

In accordance with at least one embodiment disclosed herein is the realization that a customizable eyewear product can sometimes experience undesirable distortion when fitted to a wearer's unique profile. This distortion can sometimes cause discomfort for the wearer as well as inferior optical performance of the eyewear product. At least some of the embodiments of the inventions disclosed herein enable the eyewear product to exhibit enhanced structural properties in order to prevent discomfort and to maintain preferred optical characteristics of the eyewear product.

For example, a goggle is a customizable eyewear product that can be adjusted to fit a wearer's head by adjusting a strap of the goggle. Goggle applications include skiing, motocross, underwater diving masks, and a variety of industrial safety applications such as welding and for power equipment operators. Typically, goggles offer sealed protection to the eyes and adjacent areas of the wearer's face against particulate matter or water, without providing full head protection. This geometry allows the lens to closely conform to the wearer's face and intercept light, wind, dust, etc. from directly in front of the wearer (anterior direction) and peripherally (lateral direction). Accordingly, it is quite important that they goggle closely conform to the face of the wearer during use. As such, a wearer commonly adjusts the elastic strap of the goggle to tightly press the goggle to the wearer's face.

A goggle usually comprises an arcuate unitary lens which extends across both the wearer's right and left eye fields of view. The lens can be supported by a frame, which typically surrounds the lens. The lens and the frame are both configured with a downwardly concave indent for receiving the nose. The rear surface of the frame, normally covered with a foam component or other compressible padding, is adapted to contact the wearer's face. Finally, an elastic strap is connected to the opposing lateral sides or ends of the frame in order to allow the goggle to be worn.

In use, the surface of the foam component or other compressible padding disposed at the rear of the goggle makes contact with the wearer's face. The wearer-contacting surface has a radius of curvature in the horizontal plane that is adapted to conform from side to side to the wearer's face. When the goggle is placed on a wearer with a "narrow" head, the tension from the straps extending around the back of the wearer's head can cause the lateral sides of the goggle to bend medially, thereby wrapping the goggle into a tighter radius of curvature to fit the wearer.

In many common goggles, the vertical height of the lens above the nose opening is significantly less than the vertical height of the lens in the wearer's straight ahead line of sight. Therefore, a goggle worn on a narrow head can tend to crease or bend preferentially about a vertical midline through the lens at the nose opening, especially given the rearward traction on the lateral sides of a goggle caused by the straps of the goggle. This deforms the lens geometry and creates optical distortion. This also causes a narrowing in the width of the nose opening, which in turn pinches the nose of the wearer.

Furthermore, a goggle can often exhibit severe prismatic distortion due to the bending force exerted by the strap on ends of the goggle frame to secure the goggle on the wearer's head. As noted above, the goggle can often be forced to conform to a tighter radius of curvature as the goggle conforms to the head of the wearer. Consequently, the lens mounted in the goggle frame can likewise experience deformation that results in reduced optical performance, such as optical distortion and prismatic shift.

Thus, in accordance with the present inventions, there is provided a goggle that comprises a reinforcement structure for preventing preferential bending of the goggle about the midpoint of its lens, as the lateral edges of the goggle are deflected in a medial direction. This may be accomplished, for example, by insert molding a relatively rigid support rib or element within the goggle frame, centered over the nosepiece. The length of the support rib may be less than half of the overall side to side arc length of the frame, and serves to inhibit preferential bending about the vertical midline of the goggle. Alternatively, the support may be formed within or adjacent the lower portion of the goggle frame, or may be secured directly to the lens, spanning the midline of the goggle.

In another embodiment, a goggle is provided at comprises a goggle frame, a bend control component, and a cushion component. The goggle frame can define opposing lateral portions and a central portion. The goggle frame can comprise a bridge disposed at the central portion of the goggle frame. The goggle frame can be generally flexible upon exertion of a bending force on the goggle frame. Further, the bend control component can extend along the bridge of the goggle frame. The bend control component can comprise a generally elongate body having first and second ends. The first and second ends can be disposed on opposing sides of the bridge. The bend control component can be configured to enhance flexural strength of the goggle at the bridge thereof for reducing preferential bending of the goggle frame at the bridge. Finally, the cushion component can be attached to the goggle frame and configured to be interposed between the goggle frame and a wearer's face.

In some implementations, the bend control component can be attached to the goggle frame. In this regard, the bend control component can be formed separately from the goggle frame as an insert for the goggle frame. The goggle frame can be configured to receive at least a portion of the bend control component for mounting the bend control component on the goggle frame. The bend control component and the goggle frame can also be formed from a monolithic piece of material.

The goggle frame can define an upper portion and a lower portion, and the bend control component being disposed adjacent to the upper portion of the goggle frame. Otherwise, the goggle frame can define an upper portion and a lower portion, and the bend control component being disposed adjacent to the lower portion of the goggle frame. However, it is also contemplated that the bend control component can extend along both the upper and lower edges or portions of the goggle frame.

The goggle frame can be fabricated from a first polymer and the bend control component can be fabricated from a second polymer that has a flexural strength greater than a flexural strength of the first polymer.

The goggle frame and the bend control component can be configured such that a flexural strength of the goggle at the bridge is at least equal to a flexural strength of the goggle along the lateral portions thereof. Further, the goggle frame and the bend control component can be configured such that the flexural strength of the goggle at the bridge is greater than to the flexural strength of the goggle along the lateral portions thereof.

In other implementations, the bend control component can comprise a plurality of tabs extending from the elongate body thereof. The tabs can be configured to engage respective recesses formed in the goggle frame for coupling the bend control component to the goggle frame. The tabs of the bend control component can be disposed intermediate the first and second ends thereof.

In accordance with another embodiment, a goggle is provided that comprises at least one lens, a goggle frame, and a bend control component. The goggle frame can comprise first and second lens support portions and a bridge disposed between the first and second lens support portions. The first and second lens support portions of the goggle frame can be configured to support the at least one lens in the field of view of the wearer. The bridge can form a nosepiece indentation. The goggle frame can be generally flexible in response to a bending force exerted on the bridge of the goggle frame. The at least one lens and the first lens support portion can collectively provide a first composite flexural strength. The at least one lens and the second lens support portion can collectively provide a second composite flexural strength. The at least one lens and the bridge can provide a bridge flexural strength. Finally, the bend control component can be disposed on the bridge of the goggle frame adjacent to the nosepiece indentation thereof. The bend control component can flex with the bridge of the goggle frame in response to the bending force exerted on the bridge of the goggle frame. The bend control component can provide flexural strength in addition to the bridge flexural strength to collectively provide a third composite flexural strength. In this regard, the third flexural strength can be at least equal to either of the first or second composite flexural strengths to enhance flexural strength of the goggle at the bridge to reduce preferential bending of the goggle frame at the bridge.

In some implementations, the bend control component can be formed separately from the goggle frame. The bend control component can comprise an elongate body portion that defines at least one tapering dimension. For example, a width of the bend control component can taper from a central portion thereof toward opposing ends thereof. Further, the width of the bend control component can narrow from the central portion toward the opposing ends thereof.

In other implementations, the goggle can comprise a fastener, the goggle frame can comprise a fastening cavity, and the bend control component can comprise at least one aperture. In this regard, the fastener can be configured to be seated within the fastening cavity of the goggle frame and to engage the aperture of the bend control component for attaching the bend control component to the goggle frame. In some embodiments, the goggle frame can be interposed between the fastener and the bend control component.

In accordance with yet another embodiment, a goggle is provided that comprises a bend control component, a goggle frame, and one or more engagement structures. The bend control component can comprise an elongate body and one or more engagement members disposed along the body thereof. The goggle frame can comprise a nosepiece section and an engagement recess extending along the nosepiece section. The engagement recess can be configured to receive at least a portion of the bend control component. The one or more engagement structures can corresponding to the engagement members of the bend control component. The engagement structures can be configured to secure the bend control component within the engagement recess of the goggle frame. In this embodiment, the bend control component can provide supplemental flexural strength to the goggle frame for reducing preferential bending of the frame at the nosepiece section.

In some implementations, one or more engagement members of the bend control component can comprise one or more protrusions extending from the elongate body thereof. Accordingly, one or more engagement structures can comprise one or more recesses configured to receive the one or more protrusions of the bend control component for securing the bend control component to the engagement recess of the goggle frame.

In other implementations, one or more engagement members of the bend control component can comprise one or more recesses in the elongate body thereof. Accordingly, one or more engagement structures can comprise one or more protrusions extending within the engagement recess of the goggle frame and being configured to engage with the one or more recesses of the bend control component.

Further, the one or more engagement structures can be formed monolithically with the goggle frame.

The one or more engagement structures can also comprise at least one fastener. The fastener can comprise a protrusion configured to extend through an aperture of the goggle frame and into a faster recess of the bend control component for securing the bend control component to the goggle frame. The goggle frame can also comprise a protruding member that can define an aperture. The protruding member can be receivable within the fastener recess of the bend control component for securing the bend control component to the goggle frame. Additionally, the protruding member of the goggle frame can be expandable upon insertion of the protrusion of the fastener to create interference fit between the protruding member of the goggle frame and the fastener recess of the bend control component for securing the bend control component in the goggle frame.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION

While the present description sets forth specific details of various embodiments, it will be appreciated that the description is illustrative only and should not be construed in any way as limiting. Additionally, it is contemplated that although particular embodiments of the present inventions may be disclosed or shown in the context of unitary or dual lens eyewear systems, such embodiments can be used in both unitary and dual lens eyewear systems. Further, it is contemplated that although particular embodiments of the present inventions may be disclosed or shown in the context of frames having a full orbital, whether in a goggle or sunglass, such embodiments can be used with frames having both full and partial orbitals. Furthermore, various applications of such embodiments and modifications thereto, which may occur to those who are skilled in the art, are also encompassed by the general concepts described herein.

As discussed above, many prior art goggle designs have the comment deficiency of allowing preferential bending at a midpoint of the goggle frame. Such preferential bending results in an inferior fit, reduced optical quality, and may even cause physical and optical discomfort for the wearer. Therefore, in accordance with at least one of the embodiments disclosed herein is the realization that the preferential bending of prior art goggle frames can be reduced and/or eliminated in order to enhance the comfort and performance of a goggle.

Figure 1:
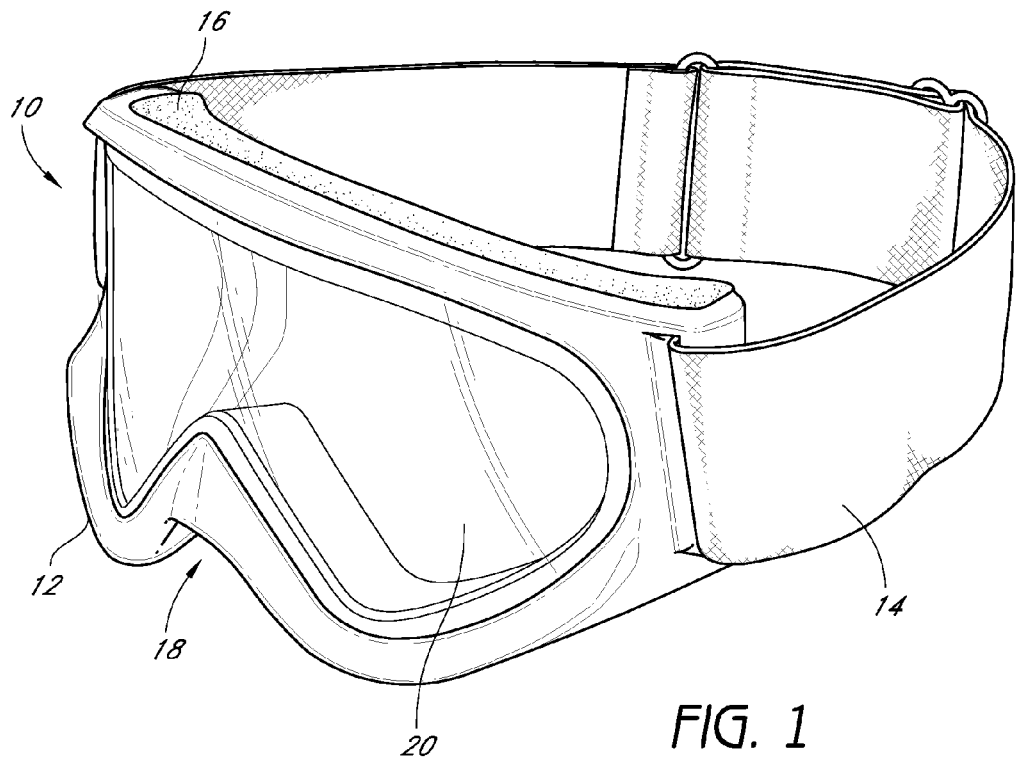
FIG. 1 is a perspective view of a prior art goggle.
Figure 3:
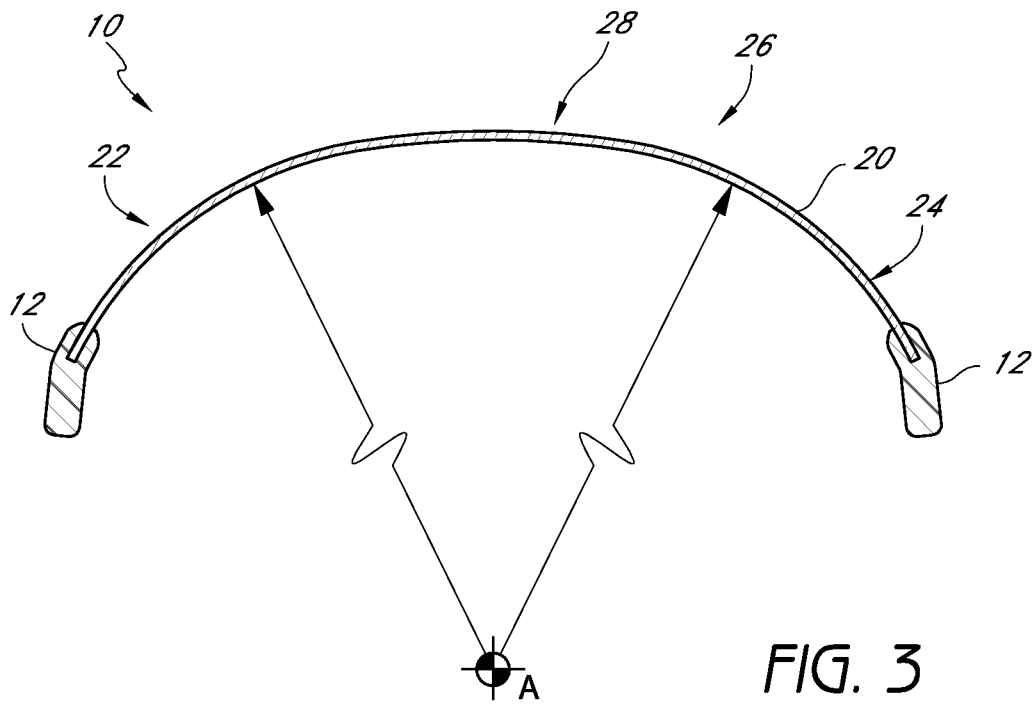
FIG. 3 is a cross-sectional top view taken along the lines 3-3 of FIG. 2.
Figure 4:
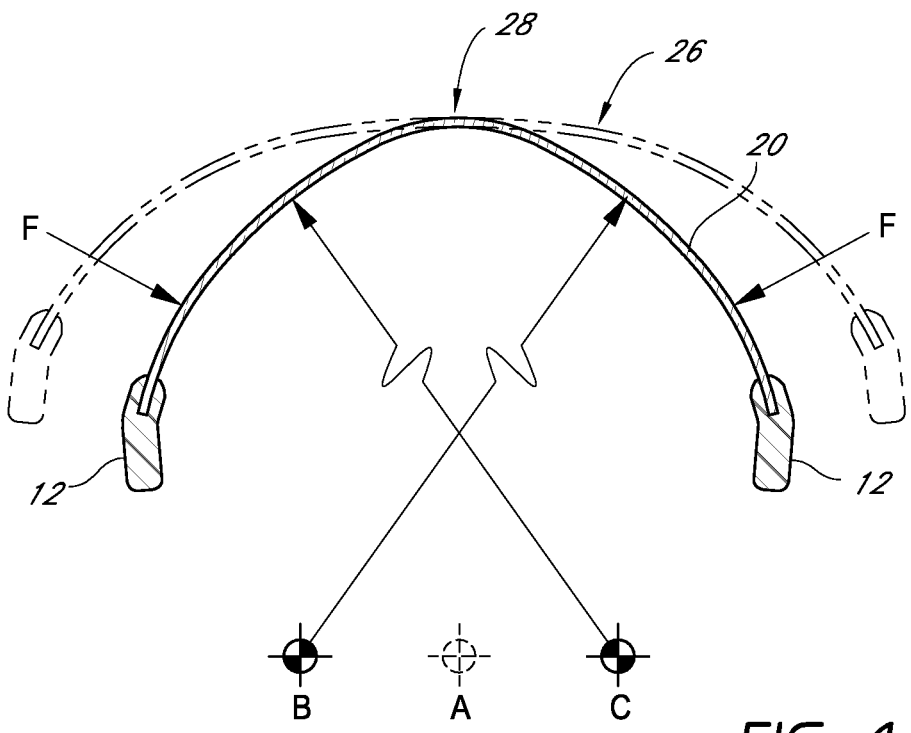
FIG. 4 is a cross-sectional top view of the goggle as shown in FIG. 3 wherein bending forces F, F are exerted on the goggle.
Figure 5:
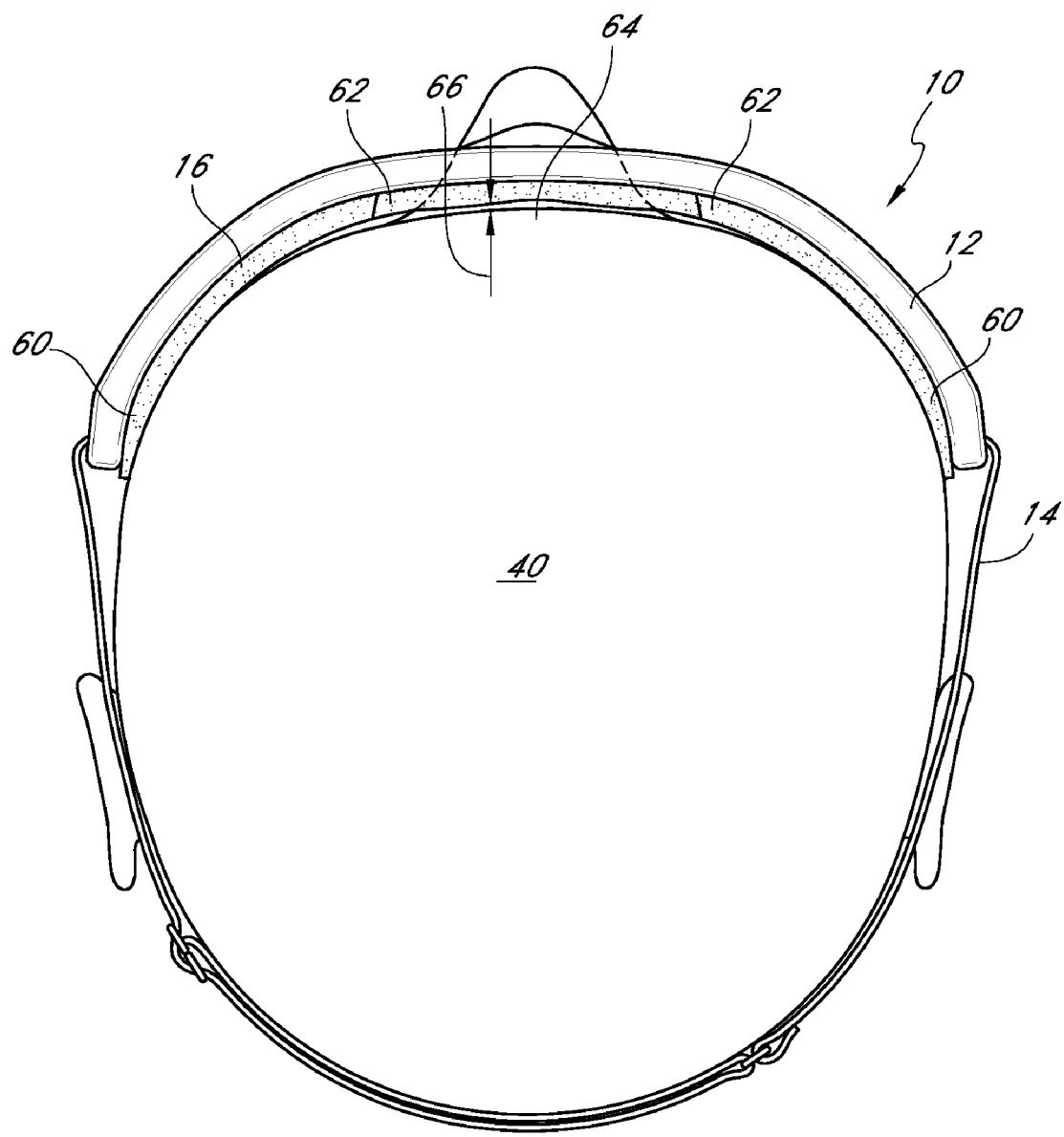
FIG. 5 is a top view of the goggle of FIG. 1 being worn on the head of a wearer.

FIGS. 1-5 illustrate a common prior art goggle design. FIG. 1 illustrates a goggle 10 that comprises a goggle frame 12, an elastic strap 14, and a foam component 16 attached to a posterior portion of the goggle frame 12. The goggle frame 12 also comprises an indent or nosepiece 18. In use, the wearer will position the goggle frame 12 onto her face and adjust the elastic strap 14 around the back of her head in order to firmly but comfortably secure the goggle frame in place. FIG. 5 illustrate a top view of a wearer's head 40 onto which the goggle 10 has been placed.

The foam component 16 is intended to contact the wearer's face and allow the goggle 10 to conform to the surface of the wearer's face. However, as discussed below, gaps can frequently be formed between the foam component 16 and the surface of the wearer's face due to the preferential bending of the goggle 10. Furthermore, the preferential bending can also cause certain portions of the foam component 16 to be highly compressed while other abortions are not compressed at all. In this regard, the foam component 16 will fail to properly distribute stresses along the surface of the wearer's face resulting in stress concentrations along side of the wearer's head, such as the sides of the forehead, temples, and cheekbones. The realization that such stress concentrations are created due to the preferential bending of the goggle frame 12 represents an aspect of at least one embodiment of the present inventions disclosed herein.

With reference to FIG. 3, a cross sectional top view of the goggle 10 is shown. As illustrated, a lens 20 of the goggle 10 is mounted in the goggle frame 12. FIG. 3 illustrates the goggle frame 12 and the lens 20 in an unloaded position. In other words, the goggle frame 12 and the lens 20 are not bent from their as-molded configuration. As such, at least lateral portions 22, 24 of the lens 20 can be configured to define a common center of curvature A in this example. In the as-molded configuration, a medial section 26 of the lens 20 defines a preferred geometry that can provide desirable optical characteristics for the goggle 10.

However, in FIG. 4, the lens 20 of the goggle 10 is shown in a loaded position. The loaded position is generally assumed when the goggle 10 is positioned on the head of the wearer. As illustrated in FIG. 4, bending forces F, F can be exerted on the lateral sides of the frame 12 and resulted in bending of the frame 12 and the lens 20. These forces F, F can be caused by the elastic strap 14 during use of the goggle 10 by the wearer.

Figure 2:
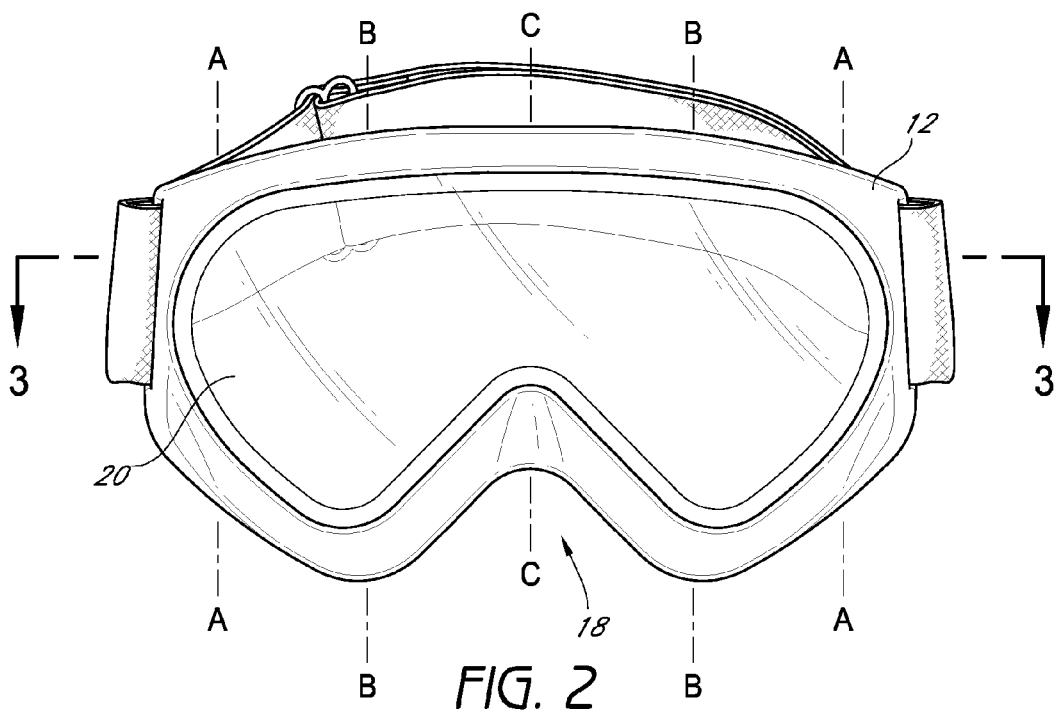
FIG. 2 is a front view of the goggle shown in FIG. 1.

When the goggle frame 12 and the lens 20 are bended in the loaded position, prior art goggles generally exhibit preferential bending at a midpoint 28 of the lens 20. In accordance with at least one embodiment disclosed herein is the realization that a disadvantage such preferential bending at the midpoint 28 of the lens 20 results in bending of the frame 12 at the nosepiece 18. As shown in FIG. 2, the nosepiece 18 has an unloaded geometry that defines a given width. Generally, the nosepiece 18 allows the wearer to comfortably position the goggle 10 on the bridge of the wearer's nose. However, preferential bending of the frame 12 will generally cause the width of the nosepiece 18 to decrease. As a result, the wearer's nose may be pinched and create discomfort for the wearer.

Additionally, the preferential bending also causes the centers of curvature of the lateral portions 22, 24 of the lens 20 to be significantly displaced from the common center of curvature A to the displaced centers of curvature B, C. The medial section 26 of the lens 20 is also significantly deformed from its unloaded position. This deformation of the lens 20 substantially worsens the original or as-molded optical characteristics of the lens 20.

For example, the lens 20 can exhibit substantial prismatic shift and other optical distortions that tend to tire the eyes of the wearer and reduce the wearer's ability to accurately perceive the position of objects. These disadvantages may not only make use of the goggle 10 uncomfortable, but can potentially affect the wearer's performance of a given activity. In fast-paced activities, such as skiing, snowboarding, skydiving, and the like, wear goggles are commonly used, the disadvantages caused by preferential bending of the lens 20 and the frame 12 can be exacerbated.

FIG. 5 illustrates yet another disadvantage of such a prior art goggle 10. The top view of FIG. 5 shows a goggle 10 that has been fitted onto a wearer's head 40. Due to the preferential bending of the goggle 10, the foam component 16 can often experience excessive compression along medial portions 60 of the foam component 16. However, more centralized portions 62 of the foam component 16 may actually be separated from the wearer's forehead 64 by a gap 66. Although the gap 66 may be minor, such gapping can be problematic in cold weather or water-related applications, such as skiing and scuba diving. In such applications, any gapping can result in impaired vision. Further, the uneven compression of the foam component 16 can create uneven stresses and stress concentrations at certain points that are exerted against the wearer's head. As a result, the wearer will generally experience greater discomfort and fatigue.

In accordance with at least one embodiment disclosed herein is the realization that the preferential bending of the goggle 10 is caused at least in part because the central section of the goggle 10 where the nosepiece 18 is located as a flexural strength that is less than the flexural strength of other portions of the goggle 10.

With reference again to FIG. 2, vertical lines A, B, C illustrate sections of the goggle 10 at which the flexural strength of the goggle 10 can be measured. The flexural strength can be defined as the ability of the goggle 10 to resist bending around a vertical axis at a given location along the goggle 10. Such bending is illustrated in FIGS. 3 and 4. Thus, the vertical lines A, B, C can represent vertical axes about which the goggle 10 can be bent at the flexural strength at that location can be measured. Additionally, the flexural strength of the goggle 10 at a given location can generally be a product of the materials and dimensions of the components used in the goggle 10 at the given location.

For example, vertical lines A are disposed adjacent to edges of opposing lateral sides of the lens 20 of the goggle 10. The flexural strength of the goggle 10 at this location may be relatively low compared to portions of the goggle 10 at vertical lines B. At vertical lines A, the lens height is neither a minimum or a maximum. However, vertical lines B are disposed along the goggle 10 generally where the lens 20 reaches a maximum height. Finally, vertical lines C are disposed along the goggle 10 generally where the lens 20 reaches a minimum height.

At each of these locations, the height of the lens 20 and the upper and lower portions of the goggle frame 12 will contribute to the flexural strength of the goggle 10. Therefore, by comparison, the flexural strength of the goggle 10 at the vertical lines B will be greater than the flexural strength of the goggle 10 at the vertical lines A and C. Additionally, the flexural strength of the goggle 10 at the vertical lines A will be greater than the flexural strength of the goggle 10 at the vertical lines C. These differences in flexural strengths result in part because of the height difference of the lens 20 at these locations. Indeed, there is less lens material available to contribute to the flexural strength of the goggle 10 at the vertical line C as compared with the vertical lines B.

As a result, the flexural strength of such a prior art goggle 10 will consistently be at a minimum at the central portion or nosepiece 18 of the goggle 10. Consequently, the bending forces experienced during normal use will cause the goggle 10 to preferentially bend at the central portion or nosepiece 18 of the goggle 10. The above-mentioned problems therefore ensue from these prior art goggles.

Therefore, in accordance with at least one embodiment disclosed herein, an improved goggle is provided that comprises a reinforced central portion configured such that the flexural strength of the central portion is at least equal to the flexural strength of other portions of the goggle. In this regard, embodiments disclosed herein will tend not to exhibit preferential bending at the central portion or nosepiece of the goggle. Specifically, some embodiments disclosed herein provide for a goggle having a central section or nosepiece section that exhibits higher relative flexural strength than other portions of the goggle. More specifically, other embodiments disclosed herein provide for a goggle having a reinforced nosepiece section that prevents undesirable bending of the goggle at the nosepiece section that otherwise results in pinching of the wearer's nose, discomfort, and lens distortion.

The central portion of the goggle can comprise a zone or section of the goggle generally extending from the straight ahead line of sight of one eye of the wearer to the straight ahead line of sight of the other eye of the wearer. In other words, the central portion of the goggle 300 can generally comprise the central one-half to two-thirds portion of the goggle.

Figure 6:
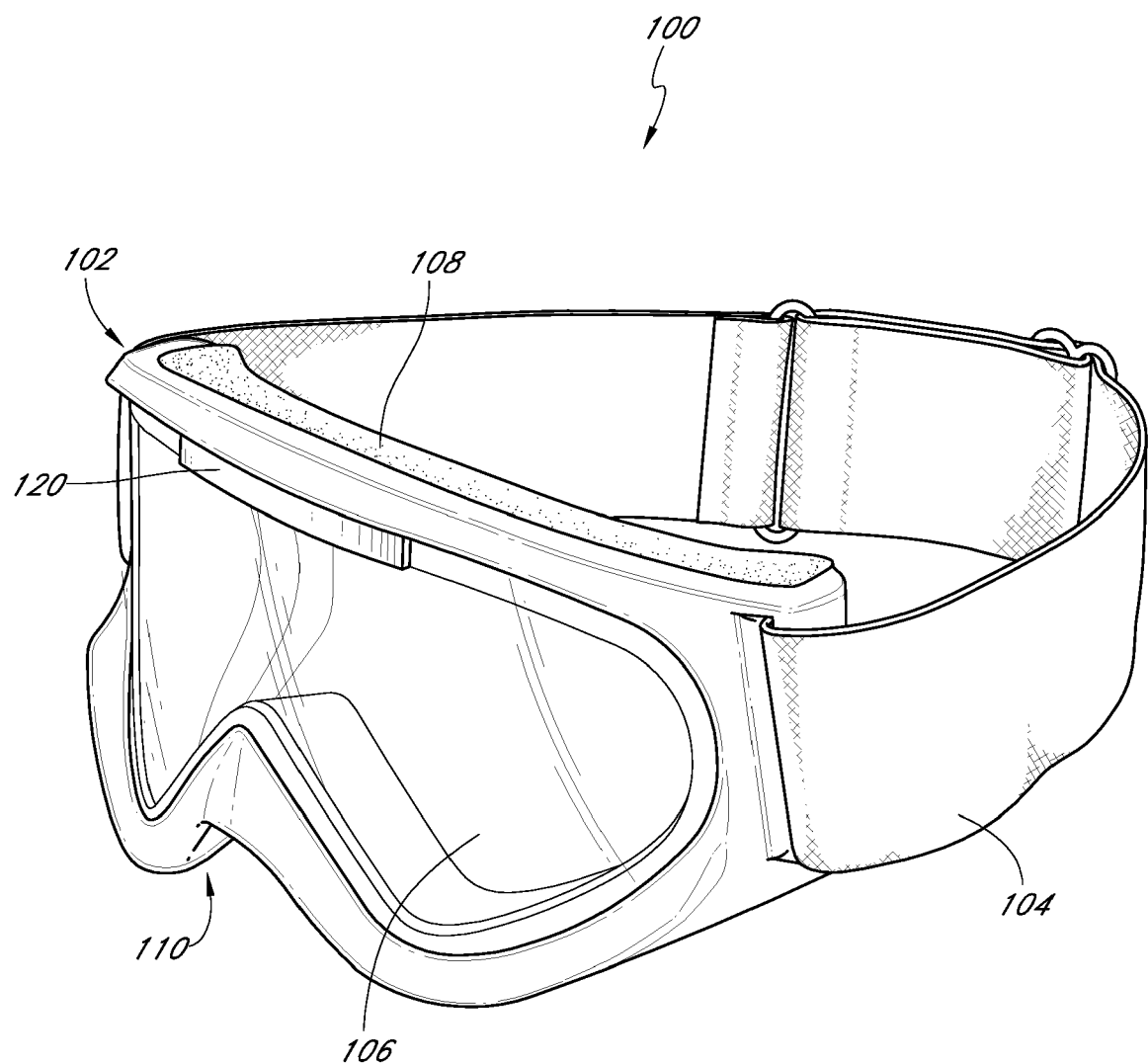
FIG. 6 is a perspective view of a goggle made in accordance with an embodiment of the present inventions.

Referring now to FIG. 6, an embodiment of an improved goggle 100 is illustrated. The goggle 100 comprises a goggle frame 102, a strap 104, at least one lens 106, and a cushion component 108. Additionally however, the goggle 100 is configured to provide bend control of the goggle frame 102 at the central portion of the goggle frame. For example, the bend control can be provided at the nosepiece indentation, bridge, or nosepiece section 110. As used herein, nosepiece indentation, bridge, or nosepiece section can refer to the feature shown as element 110. In some embodiments, the goggle frame 102 can comprise a bend control component. Such embodiments utilize the bend control component of the goggle frame 102 to provide bend resistance or additional flexural strength during normal use to mitigate and/or prevent the above-noted problems of prior art goggles, such as discomfort to the wearer and excessive lens distortion when the goggle is adjusted to fit a given wearer.

In some embodiments, the bend control of the goggle frame 102 can be implemented by adjusting one or more dimensions of the goggle frame 102. In other words, the goggle frame 102 can comprise a monolithically formed bend control component. For example, the geometry of the frame can be adjusted to compensate for decreased lens height at the central portion or nosepiece section of the goggle. Alternatively, the material from which the frame is fabricated can be varied to provide additional flexural strength at the central portion or nosepiece section of the goggle. As such, some embodiments can provide for a goggle having a central portion or nosepiece section that exhibits a generally fixed flexural strength that is greater than the flexural strength of the goggle at other locations along the goggle. Thus, such embodiments would mitigate and/or prevent preferential bending of the goggle at the central portion or nosepiece section of the goggle.

However, in other embodiments, the goggle frame 102 can comprise a separately formed bend control component that can be attached to the goggle frame 102 can provide bend control of the goggle 100. Such an embodiment is illustrated in FIG. 6. As shown, the goggle frame 102 can comprise a bend control component 120. The bend control component 120 can be attached to the goggle 100. For example, the bend control component 120 can be adhesively joined or mechanically coupled with the goggle frame 102. Further, it is contemplated that the bend control component 120 can also be a peaceably joined or mechanically coupled with other portions of the goggle 100, such as the lens 116 (with a single or double lens configuration, for example).

Figure 7:
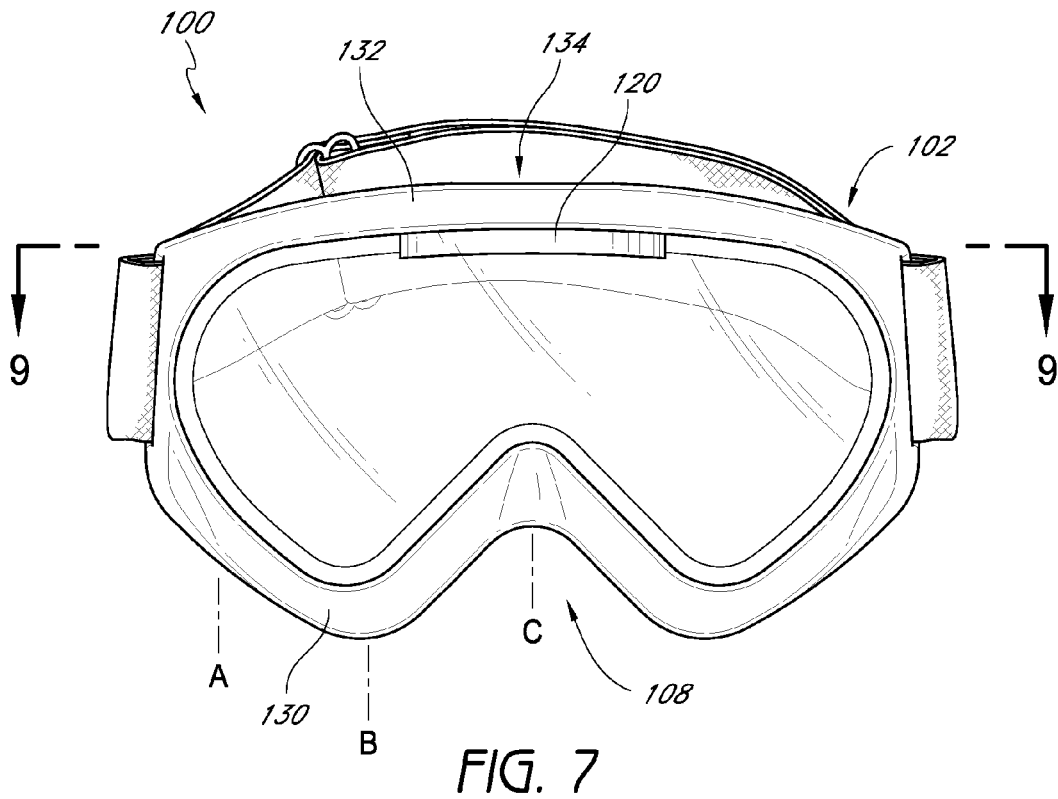
FIG. 7 is a front view of the goggle shown in FIG. 6.
Figure 8:
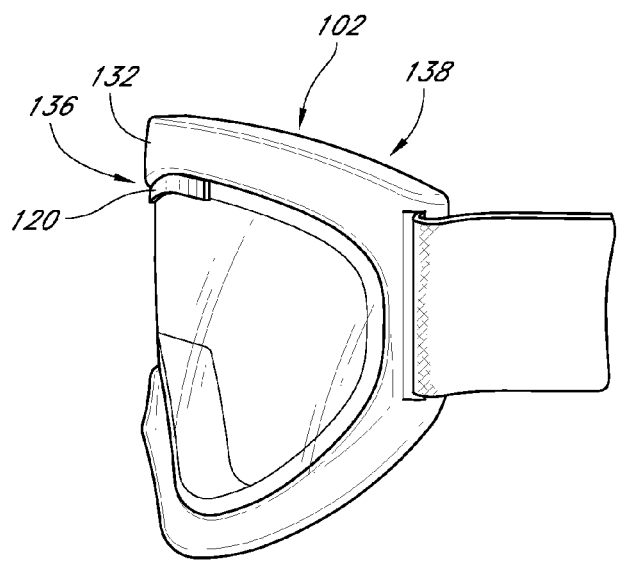
FIG. 8 is a side view of the goggle shown in FIG. 6.

FIGS. 7-8 illustrate front and side views of the embodiment of the goggle 100 shown in FIG. 6. As illustrated in FIG. 7, the lens 106 can be a unitary lens and the goggle frame 102 can be configured to surround the lens 106. As such, the goggle frame 102 can comprise a lower portion 130 and an upper portion 132. The goggle frame 102 can comprise first and second lens support portions located on either side of the nosepiece section 110. Thus, although the embodiment illustrates a unitary lens, it is contemplated that embodiments disclosed herein can also be utilized with a dual lens goggle, whether or not single or double lens layers are used.

As illustrated, the bend control component 120 can be attached to the upper portion 132 of the goggle 100. However, in other embodiments, the bend control component 120 can be attached to the lower portion 130 of the goggle frame 102. In yet other embodiments, the bend control component 120 can comprise one or more components that are attached to both of the lower and upper portions 130, 132 of the goggle 100.

In some embodiments, the bend control component 120 can extend along a central portion 134 of the goggle 100. For example, the bend control component 120 can extend between approximately 1-3 inches along the central portion 134. In embodiments where the bend control component 120 is positioned along the upper portion 132 of the goggle 100, the bend control component 120 may generally comprise an elongate straight shape. However, in other embodiments where the bend control component 120 is positioned along the lower portion 130 of the goggle 100, the bend control component 120 can also be formed in eight and one linear shape, such as an inverted V shape that generally follows the contour of the nosepiece section 110. Further, the bend control component 120 may preferably be centered relative to a centerline of the goggle frame 102.

In yet other embodiments, it is contemplated that the bend control component 120 can extend along greater than just a portion of the periphery of the goggle 100. For example, the bend control component 120 can be a retrofit component that attaches to opposing lateral sides of the goggle and extends adjacent to the perimeter of the goggle frame 102.

Additionally, as shown in FIG. 8, the bend control component 120 can be attached to an anterior portion 136 of the goggle frame 102. Nevertheless, it is contemplated that other embodiments can be configured such that the bend control component 120 is attached to a posterior portion 138 of the goggle frame 102.

Figure 9:
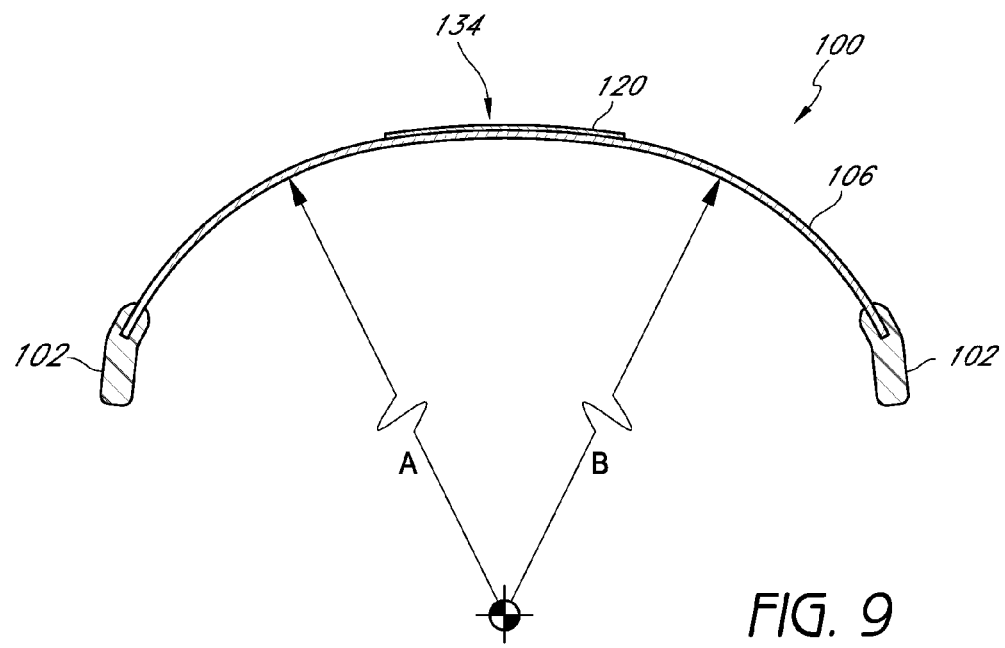
FIG. 9 is a cross-sectional top view of the goggle showed in FIG. 6.
Figure 10:
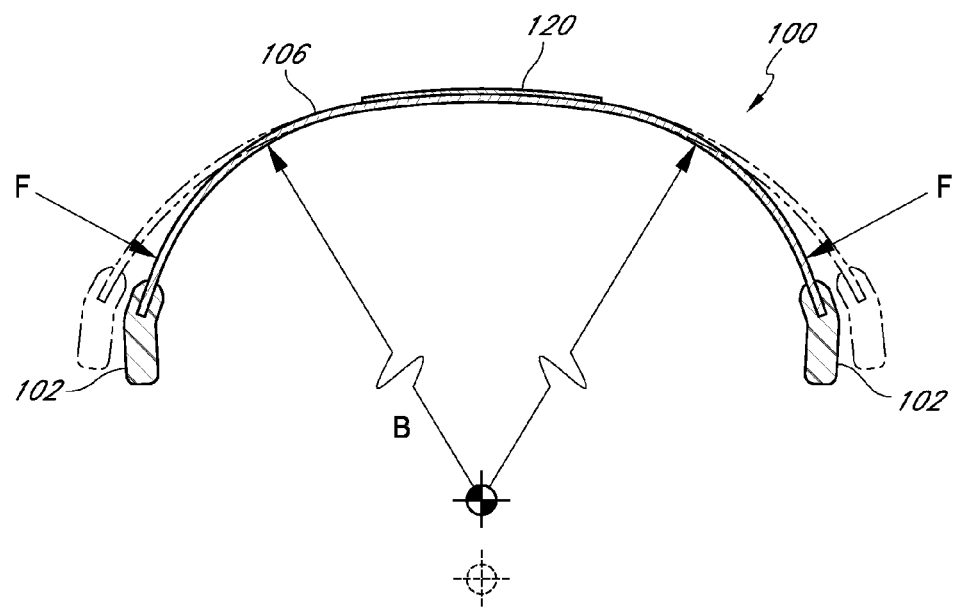
FIG. 10 is a cross-sectional top view of the goggle shown in FIG. 6 wherein bending forces F, F are exerted on the goggle.

FIGS. 9-10 illustrate cross-sectional top views of the goggle 100. In FIG. 9, the goal 100 is shown in an unloaded position. Thus, the frame 102, the lens 106, and the bend control component 120 not experiencing flexural stress resulting from use by the wearer. In some embodiments, the frame 102, the lens 106, and the bend control component 102 can be substantially free of stress in the unloaded position. However, in other embodiments, it is contemplated that the frame 102, the lens 16, and/or the bend control component 102 can be assembled in a pre-stressed condition which may aid in mitigating and/or preventing preferential bending of the goggle 100 about the central portion or nosepiece section.

FIG. 10 illustrates the goggle 100 in a loaded position. In other words, the goggle 100 is an as-worn loaded position in which forces F, F act along lateral portions of the frame 102 to cause the goggle 100 to bend. However, with the bend control component 120 in place, the goggle 100 will not tend to preferentially bend at the central portion or nosepiece section. In other words, as shown in FIG. 10, the bending of the goggle 100 will be distributed through side and lateral portions of the goggle frame 102 and the lens 106.

Accordingly, the bending of the goggle 100 in response to such forces F, F can be controlled in order to thereby mitigate and/or prevent collapse of the nosepiece opening of the nosepiece section 110 and pinching of the nose of the wearer. Further, dramatic optical distortion can also be prevented. In particular, with the bend control component 120 extending along the central portion 134 of the goggle 100, the lens 106 can tend to retain its unloaded position. Thus, the optical quality of the lens at the wearer's straight ahead line of sight may be generally undiminished from the unloaded to the loaded position.

Figure 11:
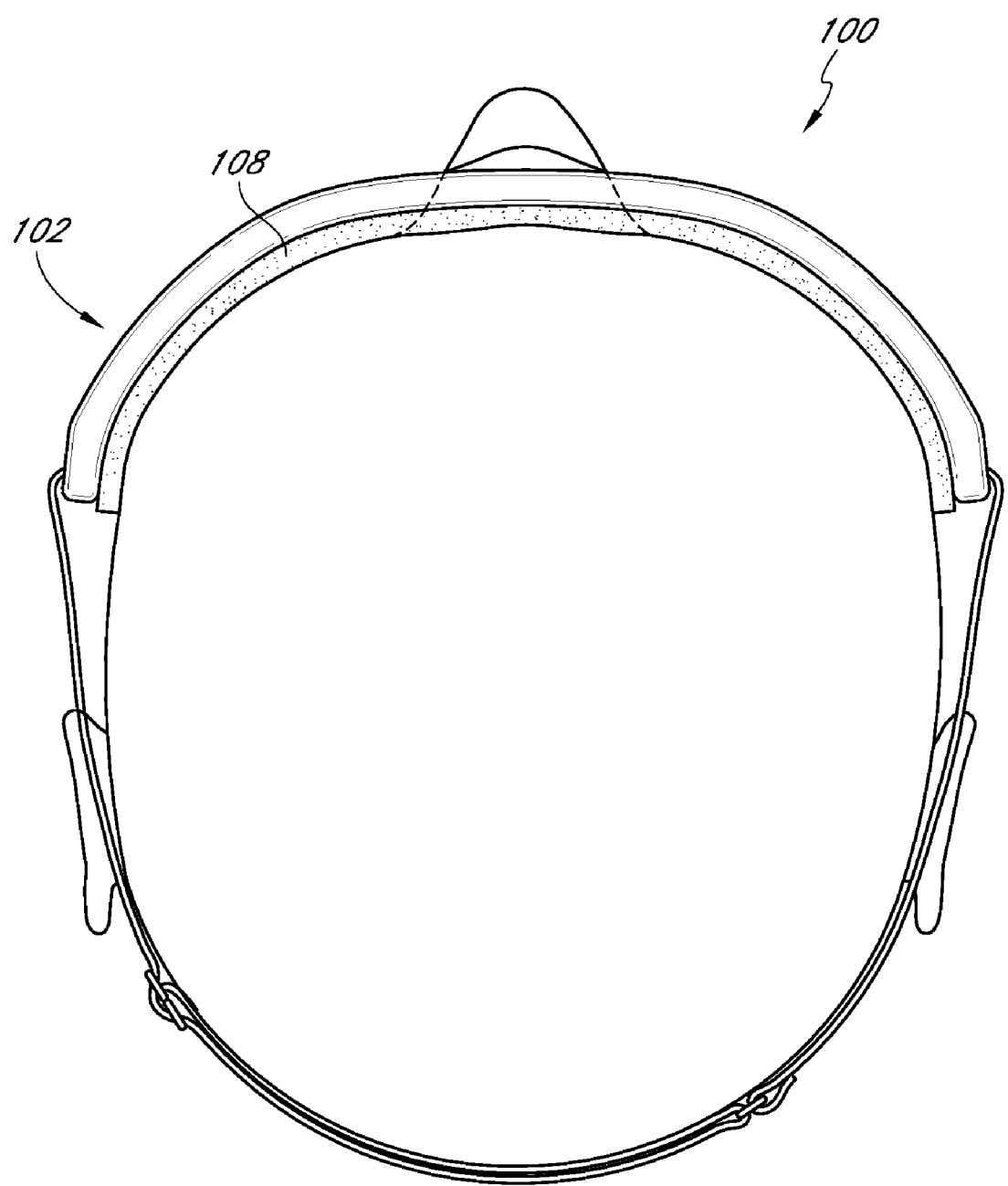
FIG. 11 is a top view of the goggle of FIG. 6 being worn on the head of a wearer.

Furthermore, FIG. 11 illustrates that in use, embodiments of the goggle can also tend to create even distribution of compressive forces through the cushion component 108. The cushion component 108 can be fabricated from a foam material or other resilient material. In other words, in contrast to the prior art goggles discussed above, embodiments of the goggles disclosed herein will not tend to create gapping between the wearer's face and the cushion component 108. Additionally, because compressive forces are evenly distributed through the cushion component 108, no stress concentrations are likely to be present that would create discomfort and fatigue for the wearer. These, and other advantages, can be obtained through implementations of various embodiments of the goggles disclosed herein.

Figure 12:
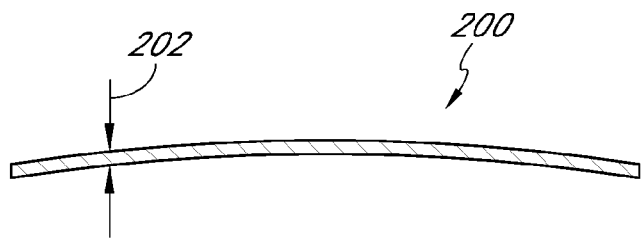
FIGS. 12-15 illustrate embodiments of a bending control component that can be incorporated into a goggle made in accordance with an embodiment of the present inventions.
Figure 13:
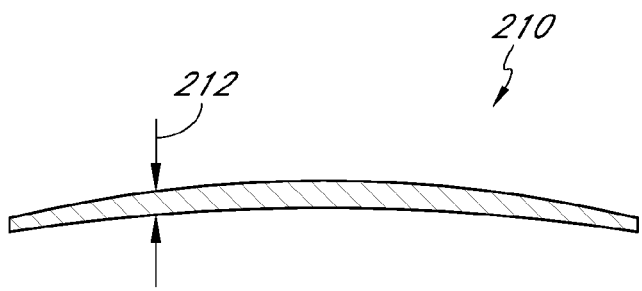
Figure 14:
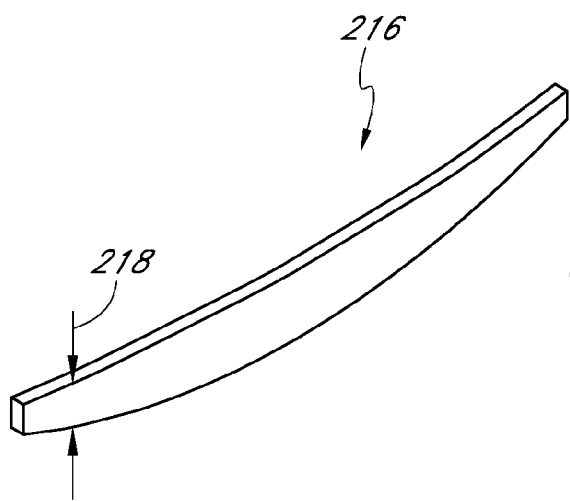
Figure 15:
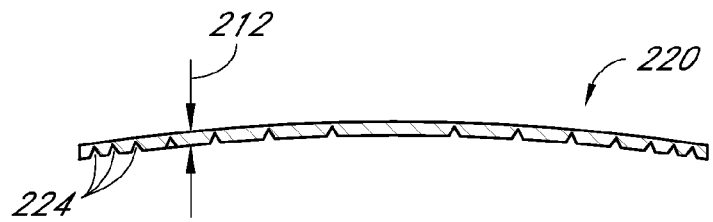

FIGS. 12-15 illustrate various embodiments of a bend control component. FIGS. 12-13 and 15 illustrate bend control components that have a constant height or vertical dimension, and therefore, only a cross-sectional top view of these components is shown in order to illustrate a width of these components. As discussed below, the bend control components shown in FIGS. 13 and 15 and a variable width that varies from a central portion thereof towards opposing ends thereof. However, as discussed below, FIG. 14 illustrates a bend control component that has a constant width and a variable height or vertical dimension that varies from a central portion thereof towards opposing ends thereof. Each of the embodiments shown in FIGS. 12-15 can provide distinct advantages and represent alternative configurations of the bend control component.

Initially however, it is noted that a goggle frame and the lens of some embodiments are configured to provide a nosepiece opening or nosepiece section. The flexural strength of the goggle varies from a centerline of the goggle toward the opposing ends thereof. Indeed, as shown in FIG. 7, the flexural strength of the goggle initially increases from section A to section B of the goggle. However, if the bend control component is not used, as in the prior art, the flexural strength of the goggle may decrease from section B to section C of the goggle.

Therefore, in accordance with at least one of the embodiments disclosed herein is the realization that the bend control component can be specifically configured to correspond with the flexural strength of the goggle at a given point or section. The flexural strength of the bend control component will be additive to the flexural strength of the goggle at a given point or section. Thus, the collective or overall flexural strength of the goggle can be represented by a summation of the individual flexural strengths of the bend control component and the goggle at a given point or section.

For example, in an implementation, the bend control component can be configured to provide a supplementary flexural strength to the central portion or nosepiece section of the goggle such that the goggle has a generally constant overall flexural strength along the central portion or nosepiece section of the goggle. In other words, while in some embodiments the bend control component can itself have a constant flexural strength along the length thereof, in other embodiments, the bend control component can be configured such that it has a variable flexural strength along the length thereof. Such a variable flexural strength can therefore correspond to and/or supplement a variable flexural strength of the central portion or nosepiece section of a goggle, and together, the central portion or nosepiece section of the goggle and the bend control component can collectively define a constant overall flexural strength. In this regard, the overall flexural strength can be defined as the sum of the flexural strength of the bend control component and the flexural strength of the goggle at a given point along the goggle; and the flexural strength of the goggle can be defined as the composite or sum of the flexural strengths of the lens and the frame at a given point along the goggle. As discussed above, in some embodiments, the overall flexural strength can advantageously be configured to prevent and/or mitigate preferential bending of the goggle at the central portion or nosepiece section thereof.

With reference now to various embodiments of the bend control component, FIG. 12 illustrates a cross-sectional top view of a bend control component 200 that has a constant cross-sectional width 202. Using the bend control component 200, the goggle would have a reinforced in flexural strength along the central portion thereof. However, although such an embodiment may prevent and/or mitigate preferential bending at the central portion or nosepiece section, it may not produce a constant overall flexural strength along the goggle.

FIG. 13 illustrates a cross-sectional top view of another embodiment of a bend control component 210 that has a variable width 212. The width 212 tapers from a central portion of the bend control component 210 toward opposing ends thereof. As a result of the variable width 212, the bend control component 210 will provide a variable flexural strength along its length. Accordingly, the bend control component 210 can be configured such that its variable flexural strength corresponds to a variable flexural strength of the goggle along the central portion or nosepiece of section thereof.

FIG. 14 illustrates a perspective view of yet another embodiment of a bend control component 216. The bend control component 216 can comprise a variable height 218. The height 218 tapers from a central portion of the bend control component 216 towards opposing ends thereof. As illustrated, the height 218 can vary along a length of the bend control component 216. However, in such an embodiment, the width of the component can be generally constant. Therefore, the variable height will allow the bend control component 216 to have a variable flexural strength along the length of the bend control component 216. As noted above, the variable flexural strength can correspond to a variable flexural strength of the goggle along the central portion or nosepiece section thereof.

FIG. 15 illustrates a cross-sectional top view of yet another embodiment of a bend control component 220 that defines a generally constant width 222, but also comprises a series of notches 224. In some embodiments, the notches can be spaced evenly along the length of the bend control component 220. However, in the illustrated embodiment, the notches 224 are spaced at decreasing intervals from the center of the bend control component 220 towards the opposing ends thereof. The notches 224 can directly affect the flexural strength of the bend control component 220 at a given point along its length. For example, the illustrated embodiment of the bend control component 220 can produce a generally variable flexural strength along the length of the component 220. Again, as noted above, the variable flexural strength can correspond to a variable flexural strength of the goggle along the central portion or nosepiece section thereof.

Figure 16:
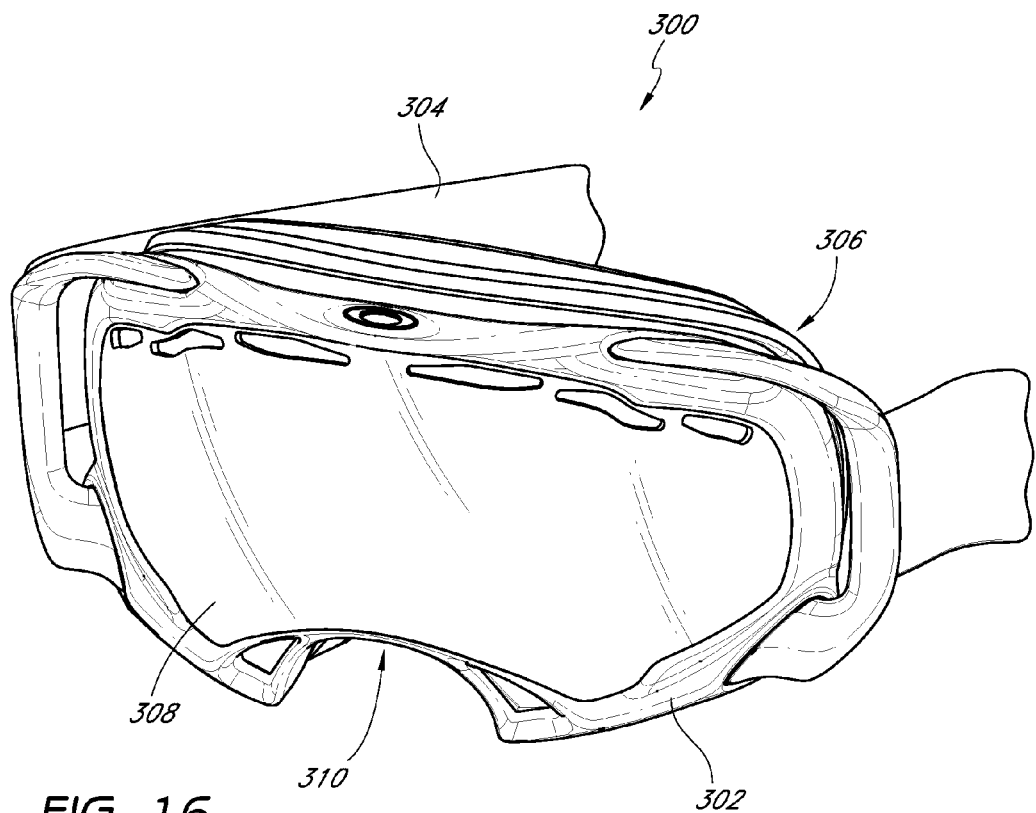
FIG. 16 is a perspective view of another goggle made in accordance with another embodiment.
Figure 17:
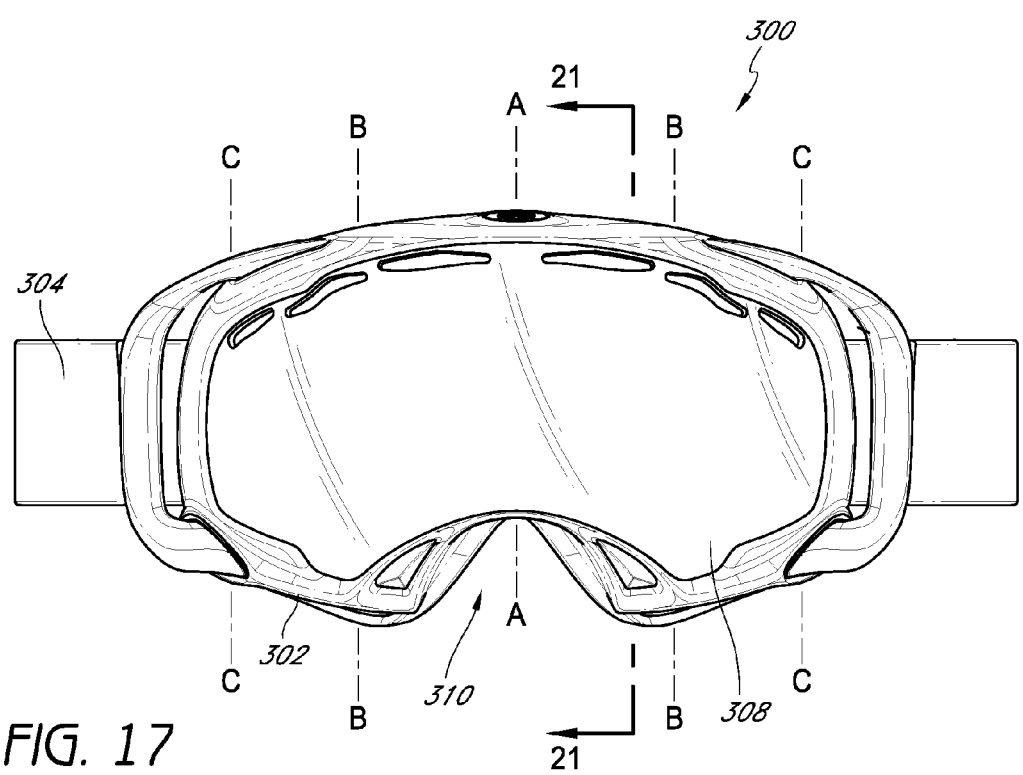
FIG. 17 is a front view of the goggle shown in FIG. 16.

FIGS. 16 and 17 illustrate yet another embodiment of a goggle 300 that can be configured to reduce and/or eliminate preferential bending of the goggle 300 at a central portion or nosepiece section thereof. The goggle 300 can comprise a goggle frame 302, a strap 304, a cushion component 306, at least one lens 308, and a nosepiece section 310 disposed along a central portion of the goggle 300. As used herein, nosepiece indentation, bridge, or nosepiece section can refer to the feature shown as element 310. The goggle frame 302 can comprise first and second lens support portions located on either side of the nosepiece section 310. Thus, although the embodiment illustrates a unitary lens, it is contemplated that embodiments disclosed herein can also be utilized with a dual lens goggle, whether or not single or double lens layers are used.

As noted above, the central portion of the goggle 300 can comprise a zone or section of the goggle generally extending from the straight ahead line of sight of one eye of the wearer to the straight ahead line of sight of the other eye of the wearer. In other words, the central portion of the goggle 300 can generally comprise the central two-thirds portion of the goggle 300.

As discussed above with respect to the embodiment illustrated in FIGS. 6-11, the embodiment shown in FIGS. 16-21 can advantageously prevent and/or mitigate this comfort to the wearer, optical distortion, and other disadvantages associated with preferential bending of the goggle at the central portion or nosepiece section thereof. The embodiment of FIGS. 16-21 illustrates a modular goggle 300 that is configured to provide bend control of the goggle to enhance the flexural strength of the goggle along the central portion or nosepiece section of the goggle.

For example, FIG. 17 illustrates vertical sections A, B, C. as discussed above with respect to the embodiment of FIGS. 6-11, the goggle 300 can be configured such that the flexural strength of the goggle 300 is not at a minimum at section A of the goggle 300. In other words, the flexural strength at sections B and C can be generally equal to or less than the flexural strength of the goggle at section A.

Figure 18:
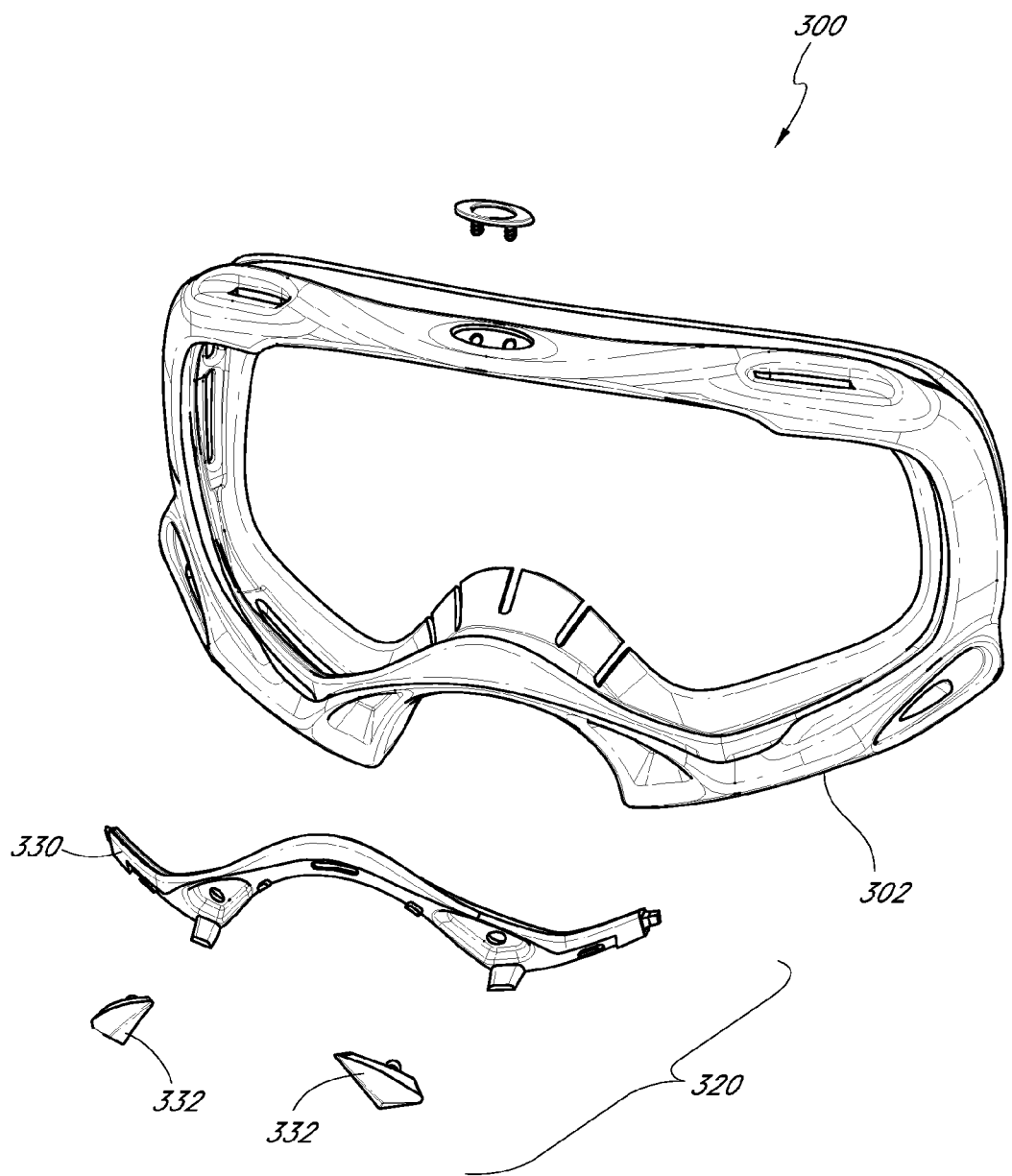
FIG. 18 is an exploded view illustrating components of the goggle shown in FIG. 16.

Referring to FIG. 18, components of the goggle 300 are shown in an exploded perspective view. In this figure, and embodiment is illustrated in which the at least one lens and foam component has been removed in order to illustrate a bend control assembly 320 and the frame 302 by themselves. Thus, in this embodiment, while it is contemplated that the lens(es) and/or the foam component can contribute to the flexural strength of the goggle, these components have been omitted to illustrate the bend control assembly 320 and the frame 302 by themselves. Further, the bend control assembly 320 can comprise at least a bend control component or insert 330. Further, in some embodiments, the bend control assembly 320 can also comprise one or more fasteners 332. For example, the illustrated embodiment utilizes both the insert 330 and the fasteners 332 with the goggle frame 302 in order to provide bend control of the goggle at the central portion or nosepiece section thereof.

Figure 19:
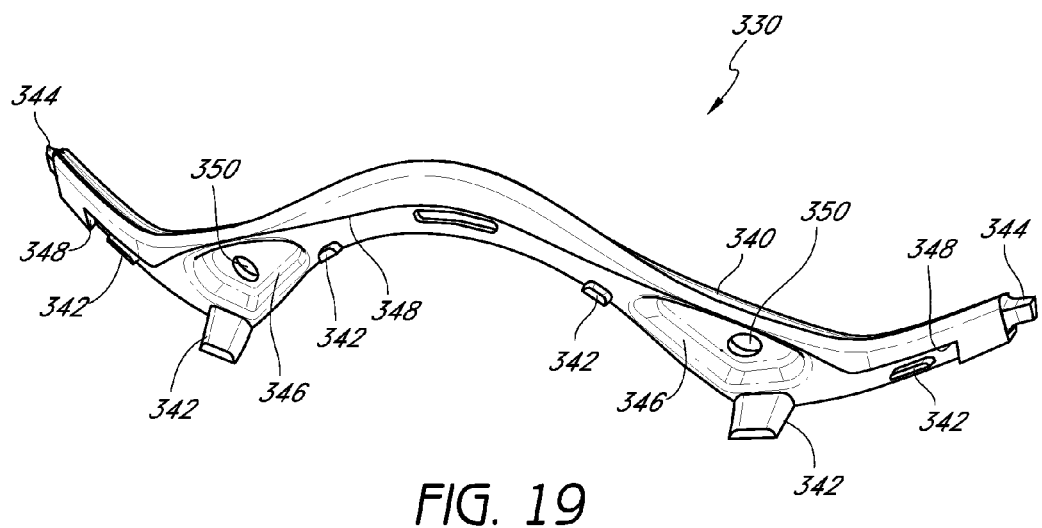
FIG. 19 is a perspective view of an embodiment of a bend control component that can be used in various embodiments of a goggle.
Figure 20:
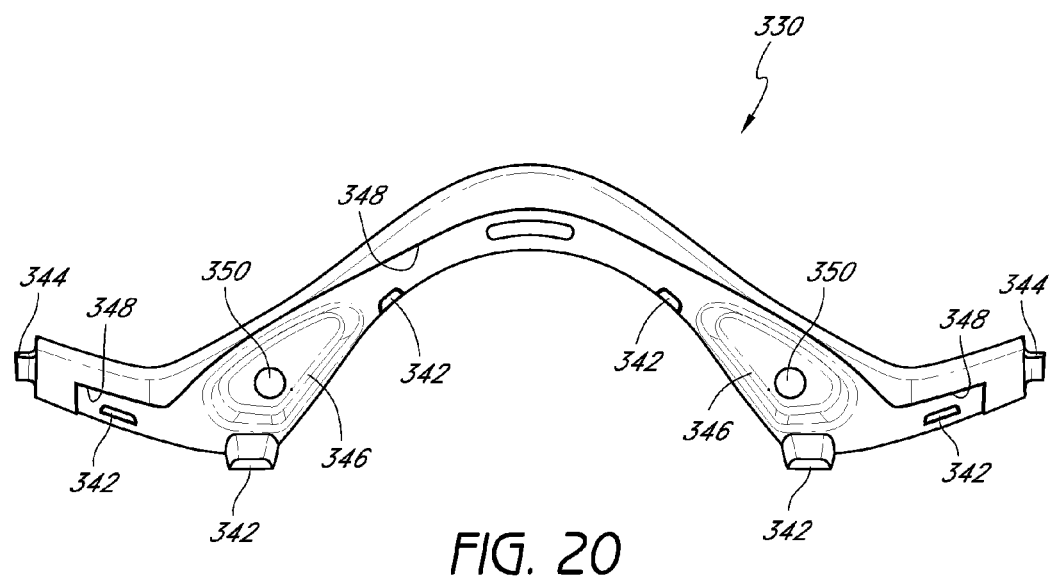
FIG. 20 is a front view of the bend control component shown in FIG. 19.

FIGS. 19 and 20 illustrate an embodiment of the bend control component or insert 330. The perspective view of FIG. 19 helps to show features and aspects of the bend control component or insert 330. As illustrated, the bend control component 330 can comprise a generally elongate body 340. Although the body 340 can define a generally linear shape, the body 340 of the illustrated embodiment defines a curvilinear shape that is configured to correspond with the curvilinear perimeter of the nosepiece section of the goggle frame. Further, as discussed herein, the bend control component 330 can be configured to be inserted to within a gap or recess of the goggle frame; accordingly, in such an embodiment, the body 340 of the bend control component 330 advantageously can generally conform to the overall shape of the nosepiece section of the goggle.

As also illustrated in FIG. 19, the bend control component 330 can comprise one or more anterior projections 342. The anterior projections 342 can be configured to engage a corresponding recess or groove of the goggle frame, as discussed below. Further, the bend control component can also comprise one or more lateral projections 344. The lateral projections 344 can be configured to engage a corresponding recess or group of the goggle frame, as also discussed below.

Although in this embodiment, the anterior projections 342 and the lateral projections 344 are used to engage corresponding portions of the goggle frame to allow the bend control component 330 to be seated at engage with the goggle frame, it is contemplated that the goggle frame could use one or more projections that engage corresponding recesses in an embodiment of the bend control component 330. In other words, the bend control component could alternatively utilize anterior and lateral recesses that engage corresponding protrusion of the goggle frame. In this regard, the illustrated embodiment of the bend control component 330 can comprise or more engagement recesses 346. The engagement recesses 346 can be configured to receive a corresponding protrusion or structure of the goggle frame for aligning and/or engaging the bend control component 330 with the goggle frame. Various other modifications or substitutions can be utilized to provide functional embodiments of the bend control component 330.

Additionally, in some embodiments, the bend control component 330 can also comprise a mating edge or shelf 348. The mating edge or shelf 348 can define a limit position for the bend control component 330 as it engages the goggle frame. Further, at some embodiments the mating edge or shelf 348 can be configured such that by limiting downward movement of the bend control component 330 relative to the goggle frame when engaged with each other, rattling due to vibration can be mitigated.

FIGS. 19 and 20 also illustrate that the bend control component 330 can comprise one or more fastener recesses 350. The fastener recesses 350 can be configured so as to be engaged by a fastener extending through the goggle frame such that the bend control component can be fixed in place relative to the goggle frame. As noted above with respect to the projections, the fastener recesses 350 could be replaced with one or more projections that could extend through a corresponding recess of the goggle frame to be gauged by a fastening component, such as a threaded nut.

Figure 21:
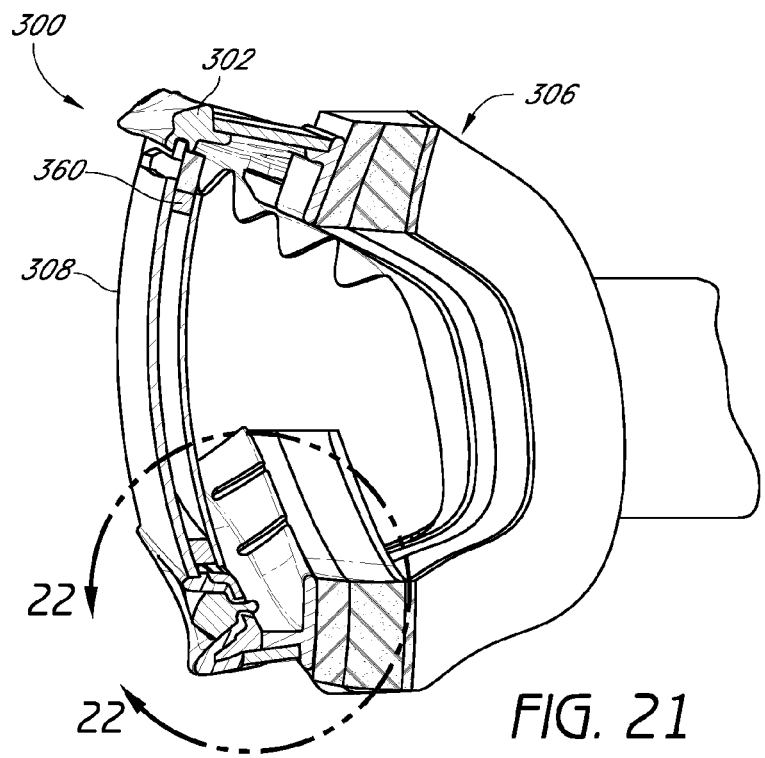
FIG. 21 is a cross-sectional side view of the goggle shown in FIG. 17, taken along section lines 21-21 of FIG. 17, according to an embodiment.
Figure 22:
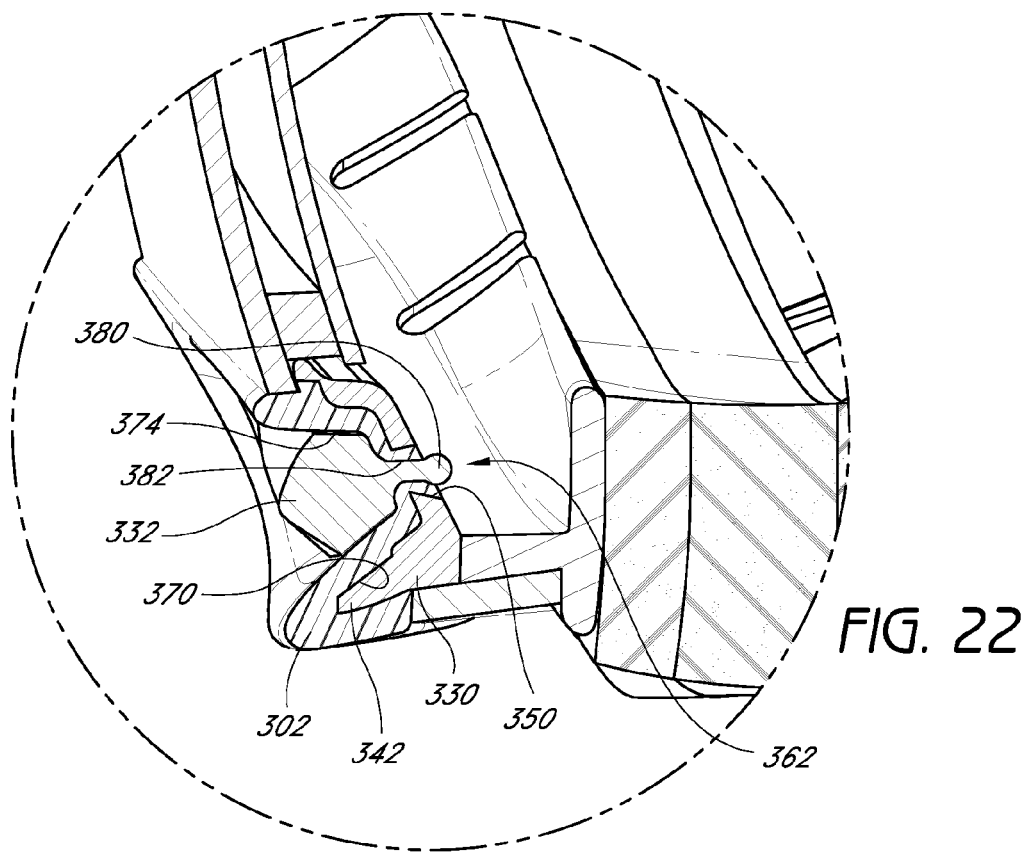
FIG. 22 is an enlarged view of a portion of the cross-sectional side view of the goggle shown in FIG. 21.

FIGS. 21-22 are cross-sectional side views of the goggle 300. These figures illustrate the alignment and engagement of the various components of the goggle 300. For example, the cross-sectional view illustrates that two unitary lenses 308 can be used in the goggle 300. The lens is 308 can be separated by a gasket 360 and mounted in the goggle frame 302. Further, FIG. 21 also illustrates that the cushion component 306 can comprise a plurality of layers. In this regard, the cushion component 306 can be fabricated from one or more types of foam materials or resilient materials.

FIG. 22 is an enlarged view of the cross-sectional view of FIG. 21. These figures illustrate an embodiment in which the bend control component 330 is received and engaged with an engagement recess of the goggle frame 302. As shown in FIG. 22, an anterior projection 342 of the bend control component can engage a corresponding recess 370 of the goggle frame 302. Further, the fastener 332 can be received and seated within an external recess 374 of the goggle frame 302. As shown, the fastener 332 can serve to secure the bend control component to the goggle frame 302.

In accordance with an embodiment, a protrusion 380 of the fastener 332 can extend through an aperture of a protruding member 382 of the goggle frame 302. Also, as shown, the protruding member 382 of the goggle frame comprises both an aperture and a posteriorly extending body. Further, FIG. 22 illustrates that the fastener recess 350 of the bend control component 330 can be configured to receive at least a portion of the protruding member 382 therein. This initial engagement between the protruding member 382 and the fastener recess 350 can provide a first degree of retention between the goggle frame 302 and the bend control component 330. Thus, even without the use of the fastener 332, the protruding member 382 of the goggle frame can be used to engage the engagement aperture 350 of the bend control component 330.

However, a unique aspect of at least one embodiments disclosed herein is that the protrusion 380 of the fastener 332 can be urged through the aperture of the protruding member 382 act cause the posteriorly extending body to expand and forcibly engage the fastener recess of the bend control component 330. In other words, the protrusion 380 of the fastener 332 can be configured to define a passing profile or outer dimension that is slightly greater than the inner profile of the aperture of the protruding member 382. Further, the protruding member 382 can comprise a resilient material that allows the protruding member 382 to expand upon insertion of the protrusion 380 into the aperture thereof. In this regard, the protruding member 382 can also comprise one or more slits that extend along the length of the posteriorly extending body of the protruding member 382. The expansion and interference fit created by insertion of the protrusion 380 into the protruding member 382 can create a second degree of retention between the goggle frame 302 and the bend control component 330.

Accordingly, after inserting the bend control component 330 into the engagement recess 362 of the goggle frame 302, the fastener 332 can be inserted into the external recess 374 of a goggle frame 302. As the fastener 332 is urged further into the external recess 374, the protrusion 380 of the fastener 332 is urged through the aperture of the protruding member 382, causing the protruding member 382 to expand and create an interference fit with the fastener recess 350 of the bend control component 330.

However, in some embodiments the fastener 332 need not create an interference fit with the protruding member 382 and the fastener recess 350. Instead, the fastener 332 can comprise a protrusion that extends through the goggle frame 302 and the fastener recess 350. The protrusion of the fastener 332 can comprise a bulbous head that resists retraction from engagement with the fastener recess 350 of the bend control component 330. However, some embodiments, it is also contemplated that the fastener 332 can comprise another component that attaches to a distal end of the protrusion of the fastener 332 once the fastener 332 is seated or received with any external recess 374 and the fastener recess 350. Thus, the fastener 332 can secure the bend control component within the engagement recess 362 of the goggle frame 302.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A goggle comprising:
a goggle frame defining opposing lateral portions and a central portion, the goggle frame comprising a bridge disposed at the central portion of the goggle frame, the goggle frame being generally flexible upon exertion of a bending force on the goggle frame, the goggle frame comprising a front frame portion and a rear frame portion spaced apart from the front frame portion, the front frame portion being configured to support a lens in a wearer's line of sight, the rear frame portion being adjustable relative to the contours of the wearer's face;
a bend control component extending along the bridge of the front frame portion and being spaced apart from the rear frame portion of the goggle frame, the bend control component comprising a generally elongate body having first and second ends, the first and second ends being disposed on opposing sides of the bridge, the bend control component being configured to enhance flexural strength of the goggle at the bridge thereof for reducing bending of the front frame portion of the goggle frame at the bridge; and
a cushion component attached to the rear frame portion of the goggle frame and configured to be interposed between the goggle frame and the wearer's face.

2. The goggle of claim 1, wherein the bend control component is attached to the front frame portion of the goggle frame.

3. The goggle of claim 2, wherein the bend control component is formed separately from the front frame portion of the goggle frame as an insert for the goggle frame, the front frame portion of the goggle frame configured to receive at least a portion of the bend control component for mounting the bend control component on the front frame portion of the goggle frame.

4. The goggle of claim 1, wherein the bend control component and the front frame portion of the goggle frame are formed from a monolithic piece of material.

5. The goggle of claim 1, wherein the goggle frame defines an upper portion and a lower portion, the bend control component being disposed adjacent to the upper portion of the goggle frame.

6. The goggle of claim 1, wherein the goggle frame defines an upper portion and a lower portion, the bend control component being disposed adjacent to the lower portion of the goggle frame.

7. The goggle of claim 1, wherein the front frame portion of the goggle frame is fabricated from a first polymer and the bend control component is fabricated from a second polymer that has a flexural strength greater than a flexural strength of the first polymer.

8. The goggle of claim 1, wherein the goggle frame and the bend control component are configured such that a flexural strength of the goggle at the bridge is at least equal to a flexural strength of the goggle along the lateral portions thereof.

9. The goggle of claim 8, wherein the goggle frame and the bend control component are configured such that the flexural strength of the goggle at the bridge is greater than the flexural strength of the goggle along the lateral portions thereof.

10. The goggle of claim 1, wherein the bend control component comprises a plurality of tabs extending from the elongate body thereof, the tabs being configured to engage respective recesses formed in the front frame portion of the goggle frame for coupling the bend control component to the goggle frame.

11. The goggle of claim 10, wherein the tabs of the bend control component are disposed intermediate the first and second ends thereof.

12. A goggle comprising:
at least one lens having a stiffness;
a goggle frame having a front frame portion and a rear frame portion spaced apart from the front frame portion, the rear frame portion being adjustable relative to the contours of a wearer's face, the front frame portion of the goggle frame being configured to support the at least one lens in the field of view of the wearer, the bridge forming a nosepiece indentation, the goggle frame being generally flexible in response to a bending force exerted on the bridge of the goggle frame; and
a bend control component disposed along the bridge of the front frame portion of the goggle frame adjacent to the nosepiece indentation thereof and generally below the at least one lens, the bend control component having a stiffness that is approximately greater than the stiffness of the at least one lens, the bend control component flexing with the bridge of the front frame portion of the goggle frame in response to the bending force exerted on the bridge of the front frame portion of the goggle frame; to enhance flexural strength of the goggle at the bridge to reduce bending of the goggle frame at the bridge.

13. The goggle of claim 12, wherein the bend control component is formed separately from the goggle frame.

14. The goggle of claim 12, wherein the bend control component comprises an elongate body portion that defines at least one tapering dimension.

15. The goggle of claim 14, wherein a width of the bend control component tapers from a central portion thereof toward opposing ends thereof.

16. The goggle of claim 15, wherein the width of the bend control component narrows from the central portion toward the opposing ends thereof.

17. The goggle of claim 12, wherein the goggle comprises a fastener, the front frame portion of the goggle frame comprises a fastening cavity, and the bend control component comprises at least one aperture, the fastener being configured to be seated within the fastening cavity of the front frame portion of the goggle frame and engage the aperture of the bend control component for attaching the bend control component to the front frame portion of the goggle frame.

18. The goggle of claim 17, wherein the front frame portion of the goggle frame is interposed between the fastener and the bend control component.

19. A goggle comprising:
a bend control component comprising an elongate body and one or more engagement members disposed along the body thereof;
a goggle frame comprising a front frame portion configured to support a lens and having a nosepiece section and an engagement recess extending along the nosepiece section, the engagement recess being configured to receive at least a portion of the bend control component, the goggle frame further comprising a rear frame portion spaced apart from the front frame portion, the rear frame portion being adjustable relative to the contours of a wearer's face;
a cushion component attached to the rear frame portion and configured to be interposed between the goggle frame and the wearer's face; and
one or more engagement structures corresponding to the engagement members of the bend control component, the engagement structures configured to secure the bend control component within the engagement recess of the front frame portion of the goggle frame;
wherein the bend control component provides supplemental flexural strength to the front frame portion of the goggle frame for reducing bending of the frame at the nosepiece section.

20. The goggle of claim 19, wherein the one or more engagement members of the bend control component comprise one or more protrusions extending from the elongate body thereof.

21. The goggle of claim 20, wherein the one or more engagement structures comprise one or more recesses configured to receive the one or more protrusions of the bend control component for securing the bend control component to the engagement recess of the goggle frame.

22. The goggle of claim 19, wherein the one or more engagement members of the bend control component comprise one or more recesses in the elongate body thereof.

23. The goggle of claim 22, wherein the one or more engagement structures comprise one or more protrusions extending within the engagement recess of the goggle frame and being configured to engage with the one or more recesses of the bend control component.

24. The goggle of claim 19, wherein the one or more engagement structures are formed monolithically with the front frame portion of the goggle frame.

25. The goggle of claim 19, wherein the one or more engagement structures comprise at least one fastener, the fastener comprising a protrusion configured to extend through an aperture of the front frame portion of the goggle frame and into a fastener recess of the bend control component for securing the bend control component to the front frame portion of the goggle frame.

26. The goggle of claim 25, wherein the front frame portion of the goggle frame comprises a protruding member defining an aperture, the protruding member being receivable within the fastener recess of the bend control component for securing the bend control component to the front frame portion of the goggle frame.

27. The goggle of claim 26, wherein the protruding member of the front frame portion of the goggle frame is expandable upon insertion of the protrusion of the fastener to create interference fit between the protruding member of the front frame portion of the goggle frame and the fastener recess of the bend control component for securing the bend control component in the front frame portion of the goggle frame.

28. The goggle of claim 1, further comprising a lens supported by the front frame portion of the goggle frame.

29. The goggle of claim 28, wherein the bend control component has a stiffness that is greater that a stiffness of the lens.

30. The goggle of claim 19, further comprising a lens supported by the front frame portion of the goggle frame.

31. The goggle of claim 30, wherein the bend control component is positioned below the lens.

32. The goggle of claim 30, wherein a stiffness of the bend control component is greater than a stiffness of the lens.

* * * * *